(12) United States Patent  (10) Patent No.: US 8,729,504 B2
Zhang  (45) Date of Patent: May 20, 2014

(54) IDENTIFICATION DEVICE FOR TIN SURFACE OF FLOAT GLASS

(75) Inventor: Zhemin Zhang, Beijing (CN)

(73) Assignee: Beijing Aoptek Scientific Co., Ltd, Beijing (CN)

( * ) Notice: Subject to any disclaimer, the term of this patent is extended or adjusted under 35 U.S.C. 154(b) by 240 days.

(21) Appl. No.: 13/380,865

(22) PCT Filed: Apr. 12, 2011

(86) PCT No.: PCT/CN2011/072657
§ 371 (c)(1),
(2), (4) Date: Jan. 3, 2012

(87) PCT Pub. No.: WO2011/134346
PCT Pub. Date: Nov. 3, 2011

(65) Prior Publication Data
US 2012/0097866 A1  Apr. 26, 2012

(30) Foreign Application Priority Data
Apr. 30, 2010  (CN) ...................... 2010 2 0182123 U

(51) Int. Cl.
*G01N 21/64* (2006.01)
(52) U.S. Cl.
USPC ....................................... 250/461.1

(58) Field of Classification Search
USPC ............................... 250/461.1, 461.2
See application file for complete search history.

(56) References Cited

U.S. PATENT DOCUMENTS

| 4,323,785 | A |  | 4/1982 | McComb et al. |
| 5,548,115 | A | * | 8/1996 | Ballard et al. ............... 250/253 |
| 2007/0002313 | A1 | * | 1/2007 | Berg et al. .................. 356/128 |
| 2012/0097866 | A1 | * | 4/2012 | Zhang ....................... 250/461.1 |

FOREIGN PATENT DOCUMENTS

| CN | 201262614 Y | 6/2009 |
| CN | 201653897 U | 11/2010 |
| JP | 2001318056 A | 11/2001 |

* cited by examiner

*Primary Examiner* — Kiho Kim
(74) *Attorney, Agent, or Firm* — AKC Patents; Aliki K. Collins

(57) ABSTRACT

An identification device for a tin surface of float glass includes an outer shell (3), a gas discharge light tube (5) and a power source. The gas discharge light tube (5) and the power source are arranged inside the outer shell (3). An irradiation window is installed on the outer shell (3) corresponding to the position of the gas discharge light tube (5). A UV light-absorbing mark (6) is provided on the inner or outer surface of the irradiation window, and the tin surface of float glass can be visually identified according to whether the mark (6) can be observed.

9 Claims, 1 Drawing Sheet

IDENTIFICATION DEVICE FOR TIN SURFACE OF FLOAT GLASS

TECHNICAL FIELD

The present invention relates to an optical detection technology for a float glass, especially to an identification device for a tin surface of the float glass.

BACKGROUND ART

At present, the forming process of float glass is completed in a tin groove to which protective gas is fed, and is specifically as follows: molten glass continuously flows into the tin groove from a tank furnace and floats on the surface of tin liquor with large relative density, and under the actions of gravity and surface tension, the molten glass is spread, flattened, hardened and cooled on the surface of the tin liquor and is then subjected to annealing and other operations to obtain a flat glass product. In the above forming process of float glass, the glass molten at high temperature floats on the tin liquor, so a certain amount of tin will infiltrate into the lower surface of the glass to turn one surface of the glass into a tin surface.

The tin-infiltrating surface of the float glass has plenty of characteristics capable of influencing further deep processing of the float glass, such as screen printing, membrane coating, curved tempering and large-area flat tempering, therefore, it is quite important to accurately determine the tin surface of the float glass.

The tin in the tin surface of the float glass exists in three valence forms, including $Sn^0$, $Sn^{2+}$ and $Sn^{4+}$. The tin element will create an excitation state after absorbing proper light energy. The excitation state, which is unstable, will rapidly decay to a ground state. And the course from the excitation state to the ground state is typically accompanied by photon radiation, i.e. the phenomenon of photoluminescence. Fluorescent light belongs to the phenomenon of photoluminescence of molecules.

A hot cathode gas discharge light tube emitting UV light is mounted inside the commercially available identification devices for the tin surface of float glass currently. In practical application, the tin surface identification device irradiates upwards from the space below the float glass, the hot cathode gas discharge light tube in the tin surface identification device emits UV light, and in accordance with the phenomenon of ultraviolet photoluminescence of the tin element in the float glass, if a surface tightly adhered to the tin surface identification device is the tin surface of the float glass, the tin surface, after being irradiated by the UV light, will rise ultraviolet photoluminescence to emit white fluorescent light, and the white fluorescent light can be seen by human eyes through looking down from the upper surface of the glass; and if the surface tightly adhered to the tin surface identification device is not the tin surface of the float glass, the tin surface will not rise ultraviolet photoluminescence and the white fluorescent light can not be seen by human eyes.

Although the existing tin surface identification device has certain detection effect, the emission of UV light by the hot cathode gas discharge light tube is accompanied by visible light that could cause interference so that the tin surface generates quite unobvious white fluorescent light effect and a detector probably needs to take a long time determining whether the white fluorescent light is generated, as a result, the detection efficiency is dramatically reduced, besides, owing to the harm of the UV light to human body, long-term observation will be adverse to physical health of the detector. Moreover, the process of generating the white fluorescent light by the irradiation of the UV light to the tin surface is transient, so the determination of a detector on the detection result will be impacted if the observation is not in time.

Invention Contents:

Accordingly, the objective of the present invention is mainly to provide an identification device for a tin surface of a float glass, which can improve the identification effect and efficiency for the tin surface of float glass.

In order to reach the objective discussed above, the technical solution of the present invention is implemented in such a manner that:

The present invention provides an identification device for a tin surface of a float glass, comprising: an outer shell, a gas discharge light tube and a power source, the gas discharge light tube and the power source are arranged inside the outer shell, an irradiation window is installed on the outer shell corresponding to the position of the gas discharge light tube, and a UV light-absorbing mark is arranged on the inner or outer surface of the irradiation window.

Further, the gas discharge light tube is a hot cathode gas discharge light tube or a cold cathode gas discharge light tube or a UV light tube.

Further, the gas discharge light tube may be in any shape.

Further, a light filter is further arranged between the gas discharge light tube and the irradiation window.

Further, the UV light-absorbing mark is arranged on the inner or outer surface of the light filter.

Further, the UV light-absorbing mark is arranged on the inner surface of the irradiation window.

Further, the mark is arranged in such a manner of printing, bonding, coating or etching.

Further, the mark may be in any shape, including figure, character, letter, number and the combination thereof.

The UV light-absorbing mark is arranged on the identification device of the present invention, and during the use of the device, owing to the absence of the irradiation of UV light, the tin surface corresponding to the position of the mark emits no white fluorescent light when the tin surface identification device irradiates the tin surface of float glass and, therefore, becomes dark so as to be in sharp contrast with the area of the surrounding, UV light-irradiating tin surface that emits white fluorescent light, hence, a user can see the mark arranged on the float glass directly to obtain more obvious identification effect for the tin surface; in addition, such a manner can avoid using of light filter by eliminating the influence of visible light on the identification result, resulting in simpler structure of the entire device and lowering the cost.

In the present invention, a cold cathode gas discharge light tube can be adopted to take the place of the traditional hot cathode gas discharge light tube, and the service life of the tin surface identification device can be dramatically prolonged because of long service life of the cold cathode gas discharge light tube. Furthermore, the light filter, arranged on the outer shell of the tin surface identification device, is capable of reflecting and absorbing the visible light emitted by the cold cathode gas discharge light tube, thus more obvious effect of white fluorescent light is formed by the tin surface.

DETAILED DESCRIPTION

The present invention is based on the basic concept that: the UV light-absorbing mark is arranged on the identification device, and owing to the absence of the irradiation of UV light, the tin surface corresponding to the position of the mark emits no white fluorescent light and, therefore, becomes dark so as to be in sharp contrast with the area of the surrounding, UV light-irradiating tin surface that emits white fluorescent light, hence, a user can see the mark arranged on the float glass directly to obtain more obvious identification effect for the tin surface.

Further detailed description about the present invention is made below with reference to the drawings and the embodiments.

Figure 1:
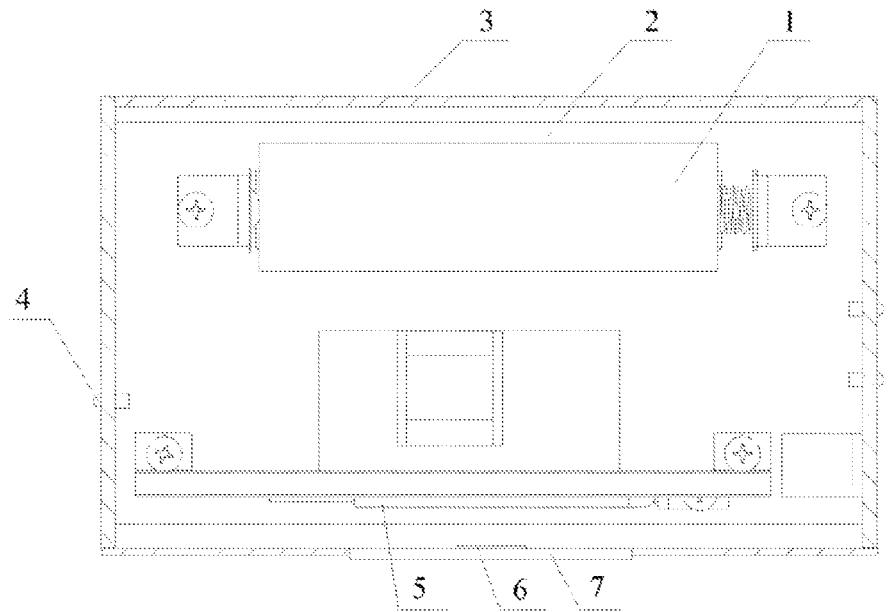
FIG. 1 is a front view of the outer shell section and the internal fundamental structure of the tin surface identification device in accordance with the present invention.

FIG. 1 is the front view of the outer shell section and the internal fundamental structure of the tin surface identification device in accordance with the present invention, shown as FIG. 1, an outer shell 3 of the tin surface identification device of the present invention mainly internally comprises: a printed circuit board 2, a lithium battery 1 arranged on the printed circuit board 2, a cold cathode gas discharge light tube 5 and the like; and a light filter 7 is arranged on the outer shell 3 corresponding to the position of the cold cathode gas discharge light tube 5. The cold cathode gas discharge light tube 5 can be randomly bent to form any various shapes.

In practical application, the cold cathode gas discharge light tube 5 is powered by the lithium battery 1 via a driver and then emits UV light, accompanied by a small amount of visible light, the light filter 7 can reflect and absorb the visible light emitted by the cold cathode gas discharge light tube 5 so that only the UV light irradiates float glass in the end. That is to say, when the tin surface identification device of the present invention is used for identifying a tin surface of float glass, the surface is determined as the tin surface if the light irradiating the float glass is white fluorescent light based on observation; otherwise, the surface is not the tin surface.

One side of the outer shell 3 of the tin surface identification device of the present invention is provided with a switch indicating lamp 4, and when the cold cathode gas discharge light tube 5 is powered by the lithium battery 1, namely, when the tin surface identification device is used, the switch indicating lamp 4 is lighted.

Also, a UV light-absorbing mark 6 can be arranged in such a manner of tightly adhering to the inner side of the light filter 7, the shape of the mark 6 can be randomly changed, for example, the forms like figure, character, letter and number can be adopted; the mark 6 can be arranged by printing, bonding, coating or etching, etc. In order to bring more convenience to use, the mark 6 is typically arranged in the center of the light filter 7. In addition, to lower the cost, the irradiation window can be provided with no light filter 7, instead, a glass sheet is used for replacing the light filter or the light filter is arranged in such a manner of tightly adhering to the inner surface of the glass sheet, and the mark 6 can be correspondingly arranged on the inner or outer surface of the glass sheet.

Figure 2:
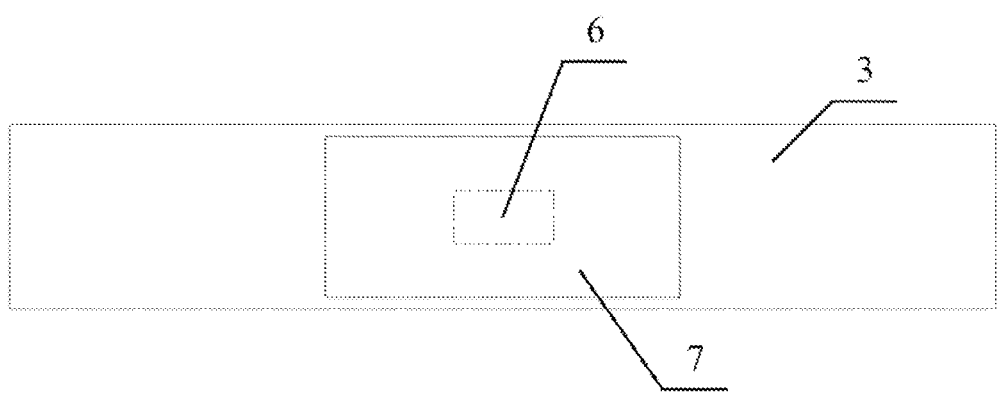
FIG. 2 is an external front view of the light filter-mounted side of the outer shell of the tin surface identification device in accordance with the present invention.

FIG. 2 is the external front view of the light filter-mounted side of the outer shell of the tin surface identification device in accordance with the present invention, in practical application, the UV light emitted by the cold cathode gas discharge light tube 5 penetrates through the light filter 7, the visible light emitted by the cold cathode gas discharge light tube 5 is reflected and absorbed by the light filter 7; the mark 6 absorbs the UV light emitted by the cold cathode gas discharge light tube 5, that is to say, the light filter 7 emits no UV light corresponding to the position where the mark 6 is arranged. In this case, owing to the absence of the irradiation of the UV light, the tin surface corresponding to the position of the mark 6 emits no white fluorescent light when the tin surface identification device irradiates the tin surface of float glass and, therefore, becomes dark so as to be in sharp contrast with the area of the surrounding, UV light-irradiating tin surface that emits white fluorescent light, hence, more obvious identification effect for the tin surface is obtained. Furthermore, the lithium battery in this embodiment can also be replaced by other available types of batteries, and the cold cathode gas discharge tube can be replaced by other available types of UV light tubes.

What is described above is merely the preferred embodiment of the present invention, not the limitation to the scope of the present invention, and any modifications, equivalent alternatives and improvements without departing from the spirit and principle of the present invention shall be contemplated as being within the scope of the present invention.

The invention claimed is:

1. An identification device for a tin surface of a float glass, comprising:
    an outer shell, a gas discharge light tube and a power source, the gas discharge light tube and the power source being arranged inside the outer shell,
    an irradiation window being installed on the outer shell corresponding to the position of the gas discharge light tube, and
    wherein a UV light-absorbing mark is arranged on a surface of the irradiation window.

2. The identification device for a tin surface of a float glass according to claim 1, wherein the gas discharge light tube is a hot cathode gas discharge light tube or a cold cathode gas discharge light tube or a UV light tube.

3. The identification device for a tin surface of a float glass according to claim 1, wherein the gas discharge light tube may be in any shape.

4. The identification device for a tin surface of a float glass according to claim 1, wherein a light filter is further arranged between the gas discharge light tube and the irradiation window.

5. The identification device for a tin surface of a float glass according to claim 1, wherein, the UV light-absorbing mark is arranged on an outer surface of the irradiation window.

6. The identification device for a tin surface of a float glass according to claim 1, wherein the UV light-absorbing mark is arranged on an inner surface of the irradiation window.

7. The identification device for a tin surface of a float glass according to claim 1, wherein the UV light-absorbing mark is arranged via printing, bonding, coating or etching.

8. The identification device for a tin surface of a float glass according to claim 1, wherein the UV light-absorbing mark may be in any shape, including figure, character, letter, number and the combination thereof.

9. An identification device for a tin surface of a float glass, comprising:
    an outer shell, a gas discharge light tube and a power source, the gas discharge light tube and the power source being arranged inside the outer shell,
    a light filter being installed on the outer shell corresponding to the position of the gas discharge light tube; and
    wherein a UV light-absorbing mark is arranged on a surface of the light filter.

* * * * *